US007679738B2

(12) United States Patent
Nagatoshi et al.

(10) Patent No.: US 7,679,738 B2
(45) Date of Patent: Mar. 16, 2010

(54) METHOD OF INSPECTING A BODY HAVING FINE-GAP GROOVES AND METHOD OF REPAIRING THE BODY

(75) Inventors: Shoichi Nagatoshi, Kariya (JP); Susumu Takahashi, Kariya (JP); Akihiko Takasu, Handa (JP)

(73) Assignee: Denso Corporation, Kariya (JP)

( * ) Notice: Subject to any disclaimer, the term of this patent is extended or adjusted under 35 U.S.C. 154(b) by 128 days.

(21) Appl. No.: 11/949,908

(22) Filed: Dec. 4, 2007

(65) Prior Publication Data
US 2008/0225302 A1 Sep. 18, 2008

(30) Foreign Application Priority Data
Dec. 4, 2006 (JP) ............... 2006-326764

(51) Int. Cl.
*G01N 21/00* (2006.01)
(52) U.S. Cl. ................................. 356/237.6
(58) Field of Classification Search .... 356/237.1–237.6
See application file for complete search history.

(56) References Cited

U.S. PATENT DOCUMENTS

| 4,988,887 | A | * | 1/1991 | Watanabe et al. ...... 250/559.16 |
| 5,906,839 | A | | 5/1999 | Miura et al. |
| 6,290,837 | B1 | | 9/2001 | Iwata et al. |
| 6,732,621 | B2 | | 5/2004 | Iwata et al. |
| 7,366,340 | B1 | * | 4/2008 | Smithgall .................... 382/141 |
| 2002/0109837 | A1 | * | 8/2002 | Goto et al. ................ 356/237.6 |
| 2002/0153356 | A1 | * | 10/2002 | Fujita et al. ............... 219/69.17 |
| 2002/0160073 | A1 | * | 10/2002 | Fukushima et al. .......... 425/380 |
| 2003/0081202 | A1 | * | 5/2003 | Yoneda .................... 356/237.6 |
| 2003/0174320 | A1 | * | 9/2003 | Yokoyama et al. ........ 356/237.6 |
| 2007/0132988 | A1 | * | 6/2007 | Gargano et al. ........... 356/237.6 |

FOREIGN PATENT DOCUMENTS

| JP | H06-258455 | 9/1994 |
| JP | H09-094813 | 4/1997 |
| JP | H11-058407 | 3/1999 |
| JP | 2001-201465 | 7/2001 |
| JP | 2004-037248 | 2/2004 |

\* cited by examiner

*Primary Examiner*—Hoa Q Pham
(74) *Attorney, Agent, or Firm*—Nixon & Vanderhye PC

(57) ABSTRACT

A molding die has through holes composed of feed holes and slit grooves for producing honeycomb structure bodies. The slit groove is formed in at least a part of each through hole. In a method of inspecting the molding die, a light is irradiated into the feed holes side to pass through the through holes. A camera is disposed at the slit groove formation side of the molding die to photograph the amount of light output from the slit groove side. A difference in intensity of the amount of light output from the slit grooves is calculated in order to detect at least the presence of a defective slit groove having an abnormal part. In another method of repairing the defective slit groove, a modifier made of abrasive grains and clay mother material is forcedly provided into the defective slit groove in order to repair or remove the abnormal part.

5 Claims, 3 Drawing Sheets

METHOD OF INSPECTING A BODY HAVING FINE-GAP GROOVES AND METHOD OF REPAIRING THE BODY

CROSS-REFERENCE TO RELATED APPLICATION

This application is related to and claims priority from Japanese Patent Application No. 2006-326764 filed on Dec. 4, 2006, the contents of which are hereby incorporated by reference.

BACKGROUND OF THE INVENTION

1. Field of the Invention

The present invention relates to a method of inspecting a body having through holes, in which a fine-gap (or narrow-gap) groove is formed in at least a part of each through hole, and relates to a method of repairing the body, specifically, repairing an abnormal part in a defective through hole. The method is applicable for inspecting and repairing various types of a body such as a honeycomb structure molding die for use of producing honeycomb structure bodies having fine-gap slit grooves.

2. Description of the Related Art

There is a molding die such as an extrusion die as an example of various types of a body having fine-gap (or narrow-gap) grooves. A monolith honeycomb type structure body (hereinafter, referred to as the "honeycomb structure body" for short) is extruded through such a molding die. The honeycomb structure body acts as a catalyst carrier of a catalytic converter for motor vehicles. The catalytic converter is mounted on an exhaust gas pipe in a motor vehicle. Through the exhaust gas pipe, the exhaust gas emitted from an internal combustion engine is flowing and purified by the catalytic converter. Such a honeycomb structure body is extruded using the molding die.

Recently, in order to improve the exhaust gas purifying function of the honeycomb structure body as an exhaust gas purifying converter and further to certainly perform the exhaust gas purifying function of the honeycomb structure body immediately after an internal combustion engine start of the motor vehicle starts, the thickness of cell walls formed in the honeycomb structure body is decreases as thin as possible. Accordingly in order to achieve the recent demand described above, the gap or interval between the adjacent slit grooves in the molding die, through which the ceramic material is extruded, is more decreased.

For example, Japanese patent NO. JP3750348 as a related art technique has disclosed the method of producing such a molding die. Through the molding die, a honeycomb structure body is extruded or produced. In the related art technique disclosed in Japanese patent NO. JP3750348, slit grooves are formed in a metal material using a thin blade grindstone as a cutting tool. Fine powder of metal generated by cutting the metal material during the slit groove formation is removed by sucking it through feed holes in order to remove fine powder of metal from the slit grooves and the feed holes in the molding die.

Because each slit groove disclosed in Japanese patent NO. JP3750348 is within a range of 105 to 110 μm, it is possible to remove the fine powder of metal by sucking from the metal material as a working material. However, as described above, because the thickness of the cell wall in the honeycomb structure body is more decreased as thin as possible, the recent demand needs having each slit groove in the molding die of a width of approximate 75 μm in a narrow dimension.

It is however difficult to completely remove the remaining fine metal of powder remained in the slit grooves and the feed holes in the molding die by sucking. As a result, the fine power of metal is still remained in the slit grooves of the molding die even if sucking is carried out during the slit groove formation. Furthermore, this causes a possibility of deform the surface of the slit grooves and feed holes through which molding material is fed and extruded in addition to choking the slit grooves with the fine powder of metal during the manufacture of the molding die. That is, the related art techniques cause the deformation in through holes (or penetrated holes) composed of fine-gap grooves (or slit grooves) and the feed holes in the molding die. It is further difficult to detect the presence of defects, namely, abnormal parts such as a deformation part and a remaining foreign matter in the slit grooves of the molding die immediately after the molding die is produced.

In the present time, the related art techniques can detect or find the presence of defects such as an abnormal part (a deformation part and fine powder of metal generated by cutting a metal material) in the molding die by inspecting a honeycomb structure body produced or extruded using the molding die in an experimental test for the molding die. In other words, the related art technique can not find the abnormal part in the molding die by directly inspecting the molding die. That is, the related art techniques detect or find the presence of defect such as a deformation part and a remaining foreign matter (remaining fine powder of metal) in the molding die using the honeycomb structure body which is produced using the molding die. Accordingly, the related art techniques must produce or extrude the honeycomb structure body in order to inspect the molding die. The molding die is then repaired or replaced with a new molding die if the presence of defect is discovered after inspecting the honeycomb structure body produced using the molding die. This causes the loss of time and production material resources in manufacture, and increasing the work in the series of production of the molding die and the honeycomb structure body.

SUMMARY OF THE INVENTION

It is an object of the present invention to provide a method capable of directly inspecting a body having fine-gap grooves, and capable of avoiding or minimizing loss of time, cost, and production material resources in manufacture of the body such as a molding die having the fine-gap grooves. The method detects a difference of the amount of light passed through the through holes (or penetrated holes) of the body. The light is irradiated into one end part of the through holes of the body and then received at the other end part of the through holes.

It is another object of the present invention to provide a method of repairing an abnormal part such as defects present in the body having the fine-gap grooves by forcedly pushing a modifier composed of abrasive particles into a defective through hole having a defective fine-gap groove in the body such as a molding die.

To achieve the above purposes, the present invention provides a method of inspecting a body having a plurality of through holes in which a fine-gap groove being formed in a part of each through hole. The method has the following steps. A light is irradiated into one end part of each through hole in order to pass through each through hole. An amount of the light passed through the through hole is measured at the other end part of each through hole. The presence of at least an abnormal part generated in the fine-gap groove in the through hole is detected and judged based on a difference of the amount of the light between the through holes. Because the method of the present invention distinguishes the difference of amount of the transparent light output from the slit grooves of the molding die, it is possible to certainly detect the presence of the abnormal part in the through hole having the fine-gap groove (the slit groove) therein.

In accordance with another aspect of the present invention, there is provided the method inspecting a molding die as the target body. The molding die is used of producing a honeycomb structure body as a catalyst carrier of a catalytic converter for motor vehicles. Each through hole has a feed hole and a slit groove. Molding material is fed through the feed holes and the molding material is extruded for producing the honeycomb structure body of a predetermined shape through the slit grooves. The method according to the present invention can inspect the molding die having fine-gap slit grooves and certainly detect the presence of the abnormal part such as remaining fine powder of metal and the deformation.

In the method according to another aspect of the present invention, the light is irradiated into one end surface side of the body in which the feed holes are formed. The light passes from the feed holes and then travels through the slit grooves. Because the transparent light is detected at the slit groove formation side of the molding die and the abnormal part easily occurs in the slit grooves, it is possible to detect the presence of the abnormal part with more certainly.

In the method according to another aspect of the present invention, each slit groove has a width of not more than 85 μm. Even if the abnormal part is generated in the slit groove having a width of not more than 85 μm, it is possible to certainly detect the presence of the abnormal part because of using the light and of detecting the abnormal part based on the difference of amount of the transparent light.

In the method according to another aspect of the present invention, the amount of light passed through the through holes is detected using a camera. It is thereby possible to certainly detect the presence of the abnormal part without overlooking it.

In the method according to another aspect of the present invention, the presence of an abnormal part generated in the through hole is judged based on a difference of the amount of light detected by the camera, and the image data regarding the abnormal part is displayed. It is thereby possible to certainly and objectively detect the presence of the abnormal part. Further, it is possible to store the image data regarding the abnormal part and to use the image data in analyzing.

In accordance with another aspect of the present invention, there is provided a method of repairing a body having through holes. In the body, a fine-gap groove is formed in at least a part of each through hole. In the method, a modifier is pushed or forcedly supplied into the through hole in which an abnormal part is present. It is thereby possible to repair and remove the abnormal part generated in at least the fine groove of the through hole with more certainly.

In accordance with another aspect of the present invention, the method modifies a molding die as the target body. The molding die is used of producing a honeycomb structure body as a catalyst carrier of a catalytic converter for motor vehicles. Each through hole has a feed hole and a slit groove. Molding material is fed through the feed holes and the molding material is extruded for producing the honeycomb structure body of a predetermined shape through the slit grooves. The method according to the present invention can repair and remove the abnormal part such as such as remaining fine powder of metal and the deformation in the molding die with certainly.

In the method according to another aspect of the present invention, the through holes without having any abnormal part are masked with a masking member and the through hole having the abnormal part is not masked, and the modifier is forcedly pushed into the slit grooves formed in a slit groove formation surface of the body through the through hole having the abnormal part. Because the slit grooves, in which the abnormal part easily occurs, are positioned at the modifier supply side, it is possible to certainly repair and remove only the defective through hole having the abnormal part, that is, to repair and remove the abnormal part using the modifier.

In the method according to another aspect of the present invention, each slit groove has a width of not more than 85 μm. It is thereby possible to certainly repair and remove the abnormal part even if the abnormal part is generated in the slit groove having a fine-gap of not more than 85 μm. In the method according to another aspect of the present invention, the modifier is made of abrasive grains and clay mother material. Because the modifier contains the clay mother material including the abrasive grains, it is possible to efficiently repair and remove the abnormal part in the defective slit groove using the friction generated between the wall of the slit groove and the modifier when compared with a case using a liquid type modifier.

In the method according to another aspect of the present invention, the abrasive grains forming the modifier is one of silicon carbide, diamond, and a mixture of silicon carbide and diamond.

Because the abrasive grains contained in the modifier is one of silicon carbide, diamond, and a mixture of silicon carbide and diamond with an adequate hardness, it is possible to certainly repair and remove the abnormal part generated in the defective slit groove of the molding die.

BRIEF DESCRIPTION OF THE DRAWINGS

A preferred, non-limiting embodiment of the present invention will be described by way of example with reference to the accompanying drawings, in which.

DETAILED DESCRIPTION OF THE PREFERRED EMBODIMENTS

Figure 1A:
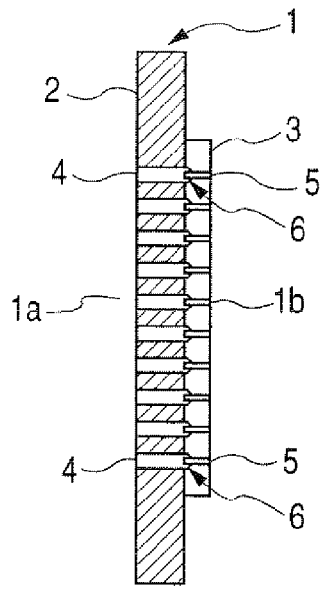
FIG. 1A is a vertical sectional view of a molding die having slit grooves (as a body having fine-gap grooves) and through which a honeycomb structure body is extruded or produced, to be inspected by a method according to an embodiment of the present invention.

Hereinafter, various embodiments of the present invention will be described with reference to the accompanying drawings. In the following description of the various embodiments, like reference characters or numerals designate like or equivalent component parts throughout the several diagrams.

Embodiment

A description will be given of a method of inspecting fine-gap grooves in a body and a method of repairing a defective fine-gap groove in the body such as a molding die (or an extrusion die) with reference to FIGS. 1A, 1B and 1C to FIG. 4. The molding die is used in an extrusion molding process for extruding or producing molding die in order to produce a honeycomb structure body.

Figure 1B:
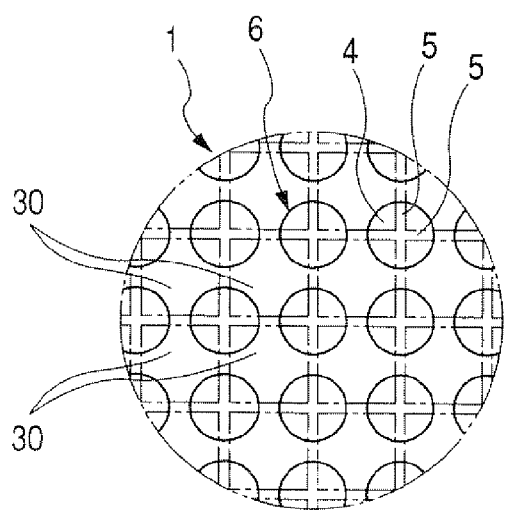
FIG. 1B is an enlarged detailed view around a center part of one surface (a feed hole formation surface) of the molding die at the left side in FIG. 1A.
Figure 1C:
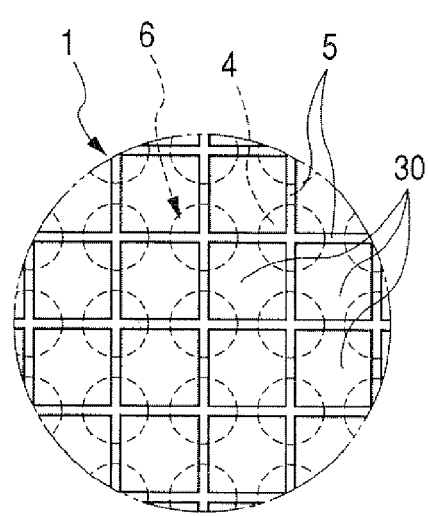
FIG. 1C is an enlarged detailed view around a center part of the other surface (a slit groove formation surface) of the molding die at the right side in FIG. 1A.

FIG. 1A is a vertical sectional view of a molding die 1 having slit grooves, as a body having fine-gap (or narrow-gap) grooves. Through the molding die 1, a honeycomb structure body is extruded or produced. The molding die 1 is a target body in inspection by the method according to the embodiment of the present invention. FIG. 1B is an enlarged detailed view around a center part of one surface 1a (as a feed hole formation surface 1a) of the molding die 1 at the left side in FIG. 1A. FIG. 1C is an enlarged detailed view around a center part of the other surface 1b (as a slit groove formation surface 1b) of the molding die at the right side in FIG. 1A.

First of all, the configuration of and how to use the molding die 1 as a body having fine-gap grooves will be explained. The molding die 1 such as an extrusion die is used for extruding, namely, producing a honeycomb structure body. The honeycomb structure body acts as a catalyst carrier of a catalytic converter or an exhaust gas purifying converter mounted on motor vehicles. The outline of the molding die 1 is approximately a square-like shape. The shape of the molding die 1 is equal or similar to the sectional shape (usually, a circular-like or an ellipse-like shape) of a honeycomb structure body of a cylinder or an elliptic cylinder because the honeycomb structure body is extruded through the molding die 1.

As shown in FIG. 1B, plural feed holes 4 are formed in the feed hole formation surface 1a (or a bottom surface) of the molding die 1, through which molding material is fed. Plural slit grooves 5 as the fine-gap grooves communicating with the feed holes 4 are formed in a lattice arrangement in the slit groove formation surface 1b as the other surface of the molding die 1. That is, the slit grooves 5 communicating with each feed hole 4 has a lattice arrangement shape in which the slit grooves 5 intersect at right angles to each other, as shown in FIG. 1C. The slit grooves 5 are formed by cutting a metal material using a thin blade grindstone or are formed by using electric discharging. According to the present invention, each through hole 6 (or each penetrated hole 6) is composed of the feed hole 4 and the slit groove 5 which are communicated together. In the embodiment according to the present invention, although the slit groove 5 is formed in a part of each through hole 6, it is acceptable that the each slit groove 5 occupies the entire of the through hole 6 in configuration.

The plurality of through holes 6 is formed in parallel to each other so that each feed hole 4 communicates with the corresponding slit groove 5 in the through hole 6. Each feed hole 4 has a diameter of approximately 0.7 mm, and each slit groove 5 has a width (or a fine-gap) within a range of 65 to 85 μm. (That is, a width measured through a center point of the slit groove 5 is 75 μm.)

About 10,000 square parts 30 are formed in the molding die 1. Those square parts 30 correspond to cells formed in the honeycomb structure body which is produced using the molding die 1. Each square part 30 is surrounded with the slit grooves 5 which are formed in vertical and horizontal directions, namely, intersect at right angles to each other in a lattice arrangement.

In the method according to the embodiment of the present inventions it is acceptable to form each part enclosed with the slit grooves 5 formed in a hexagonal-like shape or another shape instead of the square-like shape.

Figure 2A:
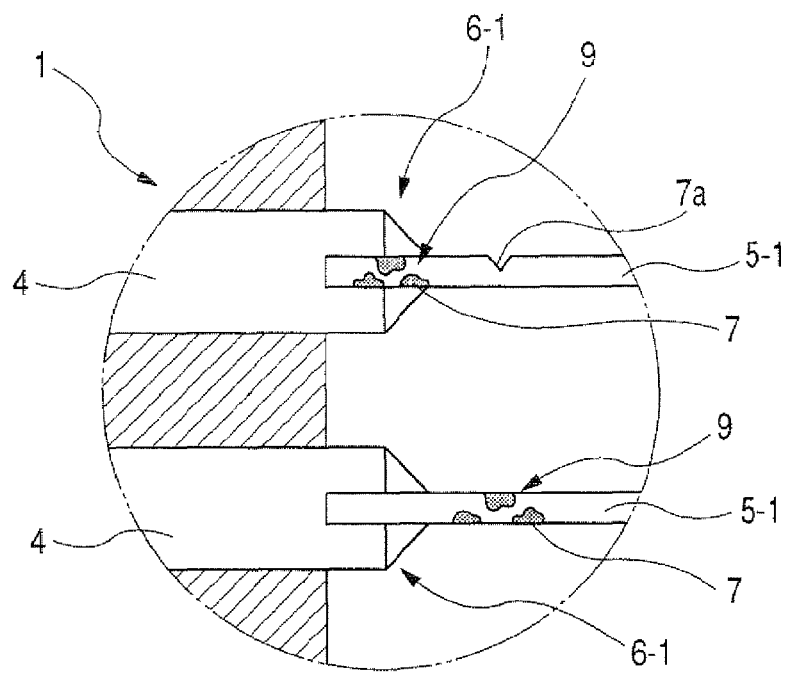
FIG. 2A is an enlarged partial sectional view of the molding die shown in FIG. 1A, as a target in inspection carried out by the method according to the embodiment of the present invention.
Figure 2B:
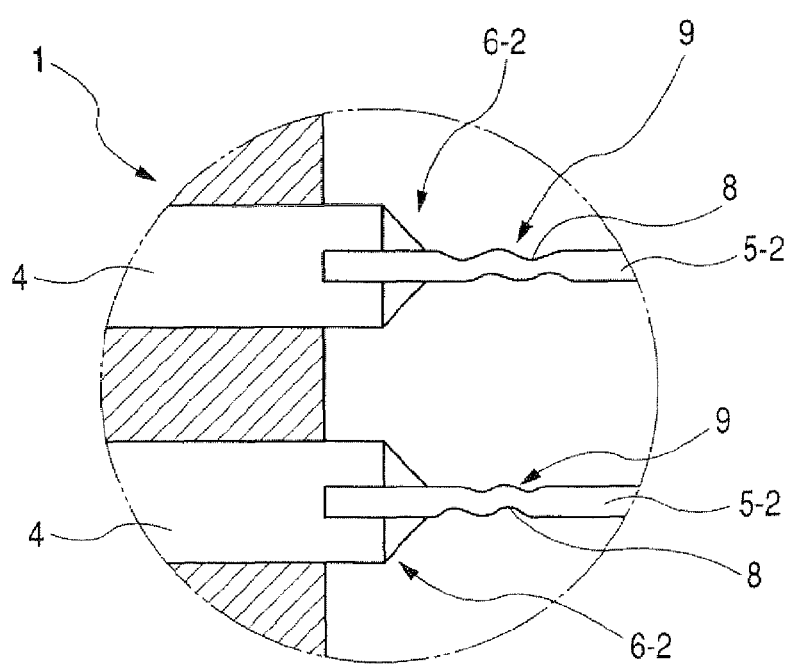
FIG. 2B is an enlarged partial sectional view of the molding die shown in FIG. 1A, as a target in inspection carried out by the method according to the embodiment of the present invention.

FIG. 2A is an enlarged partial sectional view of the molding die 1 shown in FIG. 1A, as a target in inspection carried out by the method according to the embodiment of the present invention. FIG. 2B is an enlarged partial sectional view of the molding die 1 shown in FIG. 1A, as a target in inspection carried out by the method according to the embodiment of the present invention.

As described in Japanese patent NO. JP3750348 as a related art technique, fine powder of metal (as foreign matter) is generated by cutting the metal material in order to make the slit grooves 5. The fine powder of metal is not remained in the slit grooves 5 when the width of each slit groove has a relatively wide width within a range of 105 to 110 μm, for example. On the contrary, when each slit groove 5 has a fine-gap within a range of 65 to 85 μm in the molding die 1 of the embodiment described above, there is a possibility of occurring abnormal parts 9 such as the fine powder 7 of metal remained in the slit groove 5-1 shown in FIG. 2A, a projecting part 7a formed in the slit groove 5-1 shown in FIG. 2A, and deformed parts 8 formed in the slit grooves 5-2 shown in FIG. 2B.

In the related art techniques as prescribed above, it is difficult to find or discover the presence of the abnormal parts 9 generated in the slit grooves during the manufacture of the molding die 1 because each slit groove 5 has a fine gap. That is, in the related art techniques, an inspector finds or discovers the presence of defects of the slit grooves formed in the molding die by the following manner. First, the inspector inspects the honeycomb structure body with a human visual inspection. That is the inspector does not directly inspect the molding die. As a result of the inspection, the inspector finds or discovers the presence of defects such as fine powder of metal (as foreign matter) and a deformation of the honeycomb structure body caused by a defective slit groove in the honeycomb structure body produced by using the molding die. In order to repair the abnormal part of the molding die, the related art techniques need to return the current manufacturing work to the molding-die production stage after completion of the test molding step of producing a honeycomb structure body using the molding die 1. Thus, the related art techniques cause the loss of time and production material resources in manufacture, and increase the work in the series of production of the molding die and the honeycomb structure body.

The inventors according to the present invention have found and invented the improved method of inspecting fine-gap grooves formed in a body such as the molding die 1.

A description will now be given of the method of inspecting fine-gap grooves formed in a body such as slit grooves formed in the molding die 1 through which a honeycomb structure body is extruded or produced. The method according to the present invention can detect the presence of the abnormal part 9 such as the deformation part 7a and the remaining fine powder 7 of metal, which is generated by cutting the metal material and then remained in the slit groove 5-1 communicating with the feed hole 4 in the through hole 6-1 (see FIG. 2A) of the molding die 1. In particular, the method of inspecting according to the present invention can be performed immediately after the molding die 1 is produced and before initiating the test molding of producing a honeycomb structure body using the molding die 1.

Figure 3:
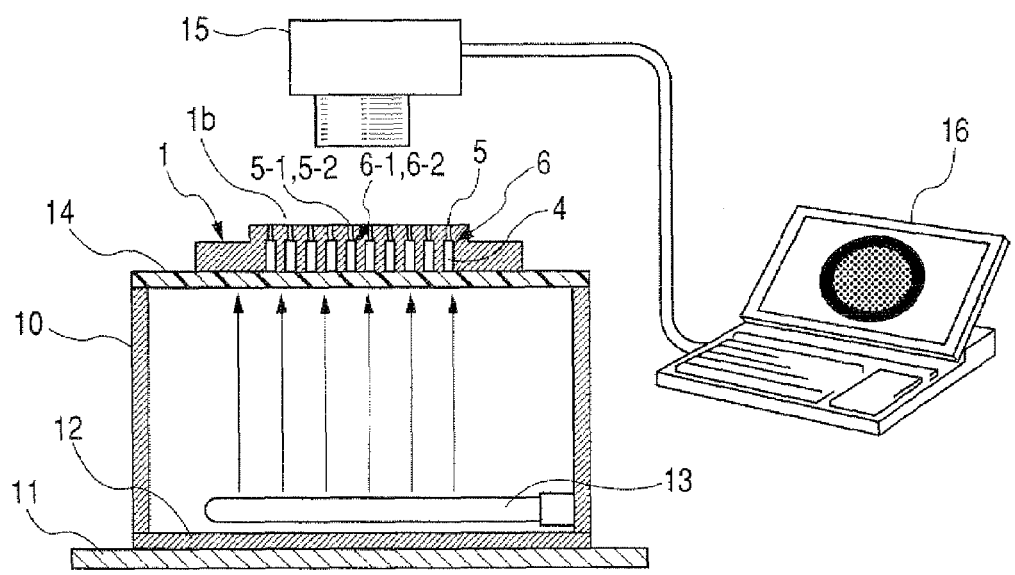
FIG. 3 is a schematic view showing a configuration of a defect inspection system for carrying out the method of inspecting the fine-gap grooves in the molding die according to the embodiment of the present invention.

FIG. 3 is a schematic view showing a configuration of a defect inspection system for carrying out the method of inspecting the slit grooves (as fine-gap grooves) in the molding die 1 according to the embodiment of the present invention.

In the defect inspection system shown in FIG. 3, a container 10 is placed on a table 11. The upper part of the container 10 is open. On the contrary, the bottom surface of the container 10 is closed. A pair of fluorescent lamps 13 is, as a light source, disposed in horizontal direction on the bottom part 12 of the container 10. A transparent or clear glass plate 14 is disposed at the upper part of the container 10. The molding die 1 is placed on the transparent glass plate 14 at the upper part of the container 10, where the silt groove formation surface 1b in which the slit grooves 5 are formed is placed as the top surface and the feed hole formation surface 1a in which the feed holes 4 are formed is placed as the bottom surface.

It is preferable to use the fluorescent lamps 13 of a large length and wide (in the longitudinal direction in FIG. 3 and in the direction perpendicular to the sheet of FIG. 3) as large as possible in order to transparent the light, which is irradiated from the fluorescent lamps 13, in parallel into all of the through holes 6. Each through hole 6 is composed of the feed holes 4 and the slit grooves 5. This condition enables all of the transparent holes 6 in the molding die 1 to be observed with a same intensity of illumination.

As shown in FIG. 3, a digital camera 15 in the defect inspection system is disposed over the top surface (the slit groove formation side) of the molding die 1. The digital camera 15 measures, namely, photographs the amount of transparent light passing through the slit grooves 5 in the slit groove formation surface 1b (the top surface of the molding die 1) from the feed holes 4 in the feed hole formation surface 1a (the bottom surface of the molding die 1). The transparent light has the image corresponding to the state of the slit grooves 5 in the molding die 1. The transparent light corresponding to the position of the slit grooves 5 is bright, and on the contrary the light corresponding to the defective slit grooves (for example, designated by reference numbers 5-1, 5-2 in FIG. 2A and FIG. 2B) other than the normal slit grooves 5 becomes (lark because the light hardly passes through the defective slit grooves 5-1, 5-2 when compared with the transparent passed through the normal slit grooves 5.

However, as has been explained above in detail with reference to FIG. 2A and FIG. 2B, the light passing through the defective slit grooves 5-1 and 5-2 in the through holes 6-1, 6-2 becomes dark when the defective slit grooves 5-1 and 5-2 have the abnormal parts 9 therein such as the remaining fine powder 7 of metal, the projecting part 7a, and the deformation part 8. Accordingly, it is possible to detect or discover the presence of the abnormal part 9 in the defective slit groove 5-1 by distinguishing the intensity of amount of the light passed through the normal slit grooves 5 and the defective slit grooves 5-1, 5-2. In the method according to the embodiment of the present invention, the light of the pair of fluorescent lamps 13 is irradiated into the feed holes 4 formed in the feed hole formation surface 1a and then output from the slit hole grooves formed in the slit groove formation surface 1b of the molding die 1, where the feed holes 4 communicate with the corresponding slit grooves 5 in the through holes 6 in the molding die 1. That is, the presence of the abnormal part 9 can be detected or discovered with more certainly when the slit groove formation surface 1b (in which the slit grooves 5 are formed and the abnormal parts 9 are present in the slit grooves 5-1, 5-2) is placed at the light detection side, namely, at the digital camera 15 side because the light is passing from the feed hole formation surface 1a to the slit groove formation surface 1b of the molding die 1.

In addition, because the method according to the present invention detects the difference in intensity of amount of the light passing through the normal slit grooves 5 and the defective slit grooves 5-1 and 5-2, the method of the present invention can certainly detect, find, or discover the presence of the abnormal part 9 even if such an abnormal part is generated in the slit grooves having a fine gap of not more than 85 μm. Further, it is possible to inspect the molding die 1 in order to find or discover the presence of the abnormal part 9 in the slit grooves 5 of the molding die 1 with a human visual inspection, and also possible to display on a display device in a computer 16 the image data regarding the abnormal part 9 photographed by the digital camera 15, as shown in FIG. 3.

When the digital camera 15 receives the amount of light passing through the normal slit grooves 5 and the defective slit grooves 5-1 and 5-2 (namely, through the normal through hole 6 and the defective through holes 6-1 and 6-2 shown in FIG. 2A and FIG. 2B) in the molding die 1, it is possible to certainly perform the inspection work without occurrence of any inspection error, for example, without overlooking the presence of the abnormal part 9. Still further, because the computer 16 can store the image data and the inspection result obtained by the digital camera 15 into a memory device, it is possible to use the image data stored in the memory device for analyzing the condition of the molding die 1. Still further, when the computer system 16 transfers such image data and inspection result stored in the memory device to another computer system located at a distant place through a network, for example, it is possible to use and recognize the image data and the inspection result by the another computer system of a distant place.

Although the body having the fine-gap grooves to be inspected by the method according to the present invention is the molding die 1 for use of producing a honeycomb structure body. Such a honeycomb structure body is used as a catalyst carrier in an exhaust gas purifying converter for mobile vehicles. The concept of the present invention is not limited by the embodiment. For example, it is possible to apply the method according to the present invention to a body of another type having fine-gap grooves. Still further, it is possible to apply the method of the present invention to a body have fine-gap grooves of a hole-like shape other than a concave-like shape. Still further, although the embodiment of the present invention described above shows the case of generating the abnormal part 9 such as the remaining fine powder 7 of metal in the slit grooves 5-1, 5-2, it is possible to apply the method of the present invention to a case in which the abnormal part 9 is generated in the feed holes 4. That is, the method according to the present invention can be applied to any case of generating the abnormal part 9 in holes such as the feed grooves, the through holes, or the feed holes.

Next, a description will now be given of the method of repairing the body such as the molding die 1 having the fine-gap grooves having an abnormal part according to the embodiment of the present invention. In the embodiment, the molding die 1 is use as a catalyst carrier in a catalytic converter or an exhaust gas purifying converter for motor vehicles. The molding die 1 has the same configuration shown in FIGS. 1A, 1B and 1C, and FIGS. 2A and 2B.

Figure 4:
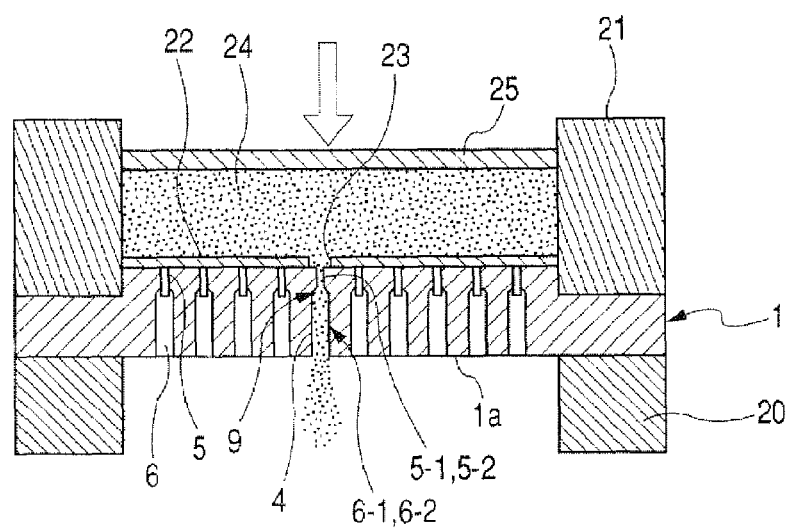
FIG. 4 is a schematic view showing a configuration of a defect repairing system for carrying out the method of repairing a defective fine-gap groove in the molding die according to the embodiment of the present invention.

FIG. 4 is a schematic view showing a configuration of a defect repairing system for carrying out the method of repairing defective fine-gap groove having the abnormal part in the molding die 1 according to the embodiment of the present invention.

The molding die 1 as the body having the fine-gap grooves is placed on a receiving tray 20 and the peripheral parts of the molding die 1 are supported on the receiving tray 20. The inside of the receiving tray 20 has a hollow part. That is, the molding die 1 is so placed on the receiving tray 20 that the feed hole formation surface 1a, in which the feed holes 4 are formed, of the molding die 1 is positioned at the bottom side and the slit groove formation surface 1b, in which the slit grooves 5 are formed, of the molding die is positioned at the top side. A pushing block 21 is placed on the molding die 1 as shown in FIG. 4. Thus, the molding die 1 is supported between the receiving tray 20 and the pushing block 21.

A masking member 22 is placed on the slit groove formation surface 1b of the molding die 1, in which the slit grooves 5 are formed. The masking member 22 masks the normal through holes 6 (composed of the feed hole 4 and the slit groove 5 communicated together) having no defect, namely without any abnormal parts 9. As shown in FIG. 4, a hole 23 is formed in the masking member 2. The hole 23 communicates with the defective through hole 6-1, 6-2 having the defect or the abnormal part 9 in the molding die 1. That is, the defective through hole 6-1, 6-2 is not covered with the masking member 22.

As shown in FIG. 4, the hollow part of the pushing block 21 is filled with a modifier 24 which is placed on the masking member 22.

The modifier 24 is a mixture of abrasive grains and clay mother material. A high polymer resin is available as the clay mother material. Silicon carbide particles, artificial diamond particles, and a mixture of them are available as abrasive grains. In the embodiment according to the present invention, the abrasion grains of a particle size within a range of 20 to 40 μm (#1,000 to #600) are used. A pushing cover 25 is placed on the modifier 24 contained in the pushing block 21. It is possible to select the particle size of the abrasive grains according to the size of the fine-gap grooves, namely, the slit grooves 5.

The process of repairing the defective slit groove 5-1, 5-2 (or the defective through hole 6-1, 6-2) having the defect part or the abnormal part in the molding die 1 is as follows.

First, a predetermined pressure is applied onto the pushing cover 25 in order to push the modifier 24. Thereby, the modifier 24 forcedly passes through the hole 23 of the masking member 22 and passes through the defective slit groove 5-1, 5-2 and the feed hole 4 of the molding die 1 to the outside of the molding die 1.

Thus, while the modifier 24 forcedly passes through the normal slit groove 5 and the defective slit grooves 5-1 and 5-2, the abrasive grains in the modifier 24 push the remaining fine powder 7 of metal remained in the slit groove 5-1 (shown in FIG. 2A), repair the projecting part 7a in the slit groove 5-1 (shown in FIG. 2A), and repair the deformed parts 8 formed in the slit grooves 5-2 (shown in FIG, 2B). By pushing the modifier 24 into the through holes 6, 6-1, 6-2 communicating with the slit grooves 5, 5-1, 5-2 and the feed hole 4 in the molding die 1, it is possible to completely repair the abnormal part 9 such as the remaining fine powder 7 of metal, the projecting part 7a, and the deformation part 8 in the slit grooves 5-1 and 5-2.

According to the method of repairing the abnormal part in the body having fine-gap grooves, because the modifier passes through the slit groove from the slit groove formation surface side of the molding die on which the through hole having no abnormal part is masked with the masking member, it is possible to repair only the through hole having the defective slit groove in which the abnormal part occurs. Further, because the slit grooves are formed in the slit groove formation surface from which the modifier is forcedly supplied into the inside of the molding die, the modifier firstly passes through the defective slit groove having the abnormal part, it is possible to certainly repair the abnormal part as a defect part in the defective slit groove.

The method according to the present invention uses the molding die having the slit grooves of a width of not more than 85 μm as a target body in inspection and modification. Even if the abnormal part is generated in the slit groove as such a fine-gap groove, it is possible to certainly repair, and remove the abnormal part in the molding die because the modifier is forcedly supplied through the defective slit groove where the abnormal part occurs.

Still further in the method of repairing the molding die according to the present invention, because the clay material is used as the mother material for the modifier, it is possible to push the modifier into the slit groove with an optimum friction which is generated between the wall of the slit groove and the modifier when compared with a case using a liquid type modifier. This can efficiently repair and remove the abnormal part in the slit groove of the molding die.

Still further, in the method of repairing the molding die according to the present invention, because the method uses silicon carbide grains, artificial diamond grains, or a mixture of silicon carbide grains and artificial diamond grains as abrasive grains in the modifier, it is possible to certainly repair and remove the abnormal part generated in the defective slit groove of the molding die with an adequate hardness of the abrasive grains in the modifier.

The embodiment described above uses the molding die as the target body having fine-gap grooves to be repaired by the method according to the present invention, and the molding die is used as a catalyst carrier in an exhaust gas purifying filter mounted on motor vehicles. However, the concept of the present invention is not limited by the cases described above, it is possible to apply the feature of the method of repairing the abnormal part in the target body according to the present invention to various types of bodies having fine-gap grooves. In addition, although the fine-gap groove has a concave-like shape in the embodiment described above, it is possible to have another shape such as a hole-like shape instead of the concave-like shape. Furthermore, in the embodiment described above, although the method is applied to the abnormal part such as the fine powder of metal generated in the slit groove of the molding die, it is possible to apply the method of the present invention to a case where the abnormal part is generated in the feed holes in the molding die. The method of repairing the abnormal part according to the present invention can be applied to various types of bodies having fine-gap grooves such as the through hole.

While specific embodiments of the present invention have been described in detail, it will be appreciated by those skilled in the art that various modifications and alternatives to those details could be developed in light of the overall teachings of the disclosure. Accordingly, the particular arrangements disclosed are meant to be illustrative only and not limited to the scope of the present invention which is to be given the full breadth of the following claims and all equivalent thereof.

What is claimed is:

1. A method of inspecting a molding die for producing a honeycomb structure body of a predetermined shape, the molding die having a plurality of through holes formed in parallel to each other, each through hole being comprised of a feed hole and a slit groove having a flow through passage smaller than a flow through passage of said feed hole, wherein a molding material is fed through the feed holes to extrude the molding material through the slit grooves during the production of the honeycomb structure body, the method comprising steps of:

irradiating parallel light from a feed hole side of the molding die toward a slit groove side of each of the through holes so that the parallel light passes in parallel through all of the through holes;

measuring, at the slit groove side of the molding die, an amount of the light passed through at least some of the through holes;

detecting the presence of an abnormal part in at least one slit groove of the plurality of through holes irradiated based on a difference in the amount of light measured for the respective through holes.

2. The method of inspecting a molding die according to claim 1, wherein each slit groove in the molding die has a width of not more than 85 μm.

3. The method of inspecting a molding die according to claim 1, wherein the quantity of the parallel light passed through the through holes is measured using a camera.

4. The method of inspecting a molding die according to claim 3, wherein the presence of a defective slit groove in the through hole is detected based on a difference of the amount of the parallel light detected by the camera, and wherein image data corresponding to the defective slit groove in the through hole is displayed.

5. The method according to claim 1, wherein the parallel light is emitted by a fluorescent lamp.

* * * * *